United States Patent [19]

Eicken et al.

[11] 4,321,395

[45] Mar. 23, 1982

[54] PREPARATION OF ACETANILIDES

[75] Inventors: Karl Eicken, Wachenheim; Wolfgang Rohr, Mannheim; Friedrich Linhart, Heidelberg, all of Fed. Rep. of Germany

[73] Assignee: BASF Aktiengesellschaft, Fed. Rep. of Germany

[21] Appl. No.: 40,224

[22] Filed: May 18, 1979

[30] Foreign Application Priority Data

Jul. 13, 1978 [DE] Fed. Rep. of Germany ....... 2830764

[51] Int. Cl.³ .................. C07D 233/20; C07D 257/04; C07D 207/10; C07D 249/02
[52] U.S. Cl. .................................. 548/253; 548/262; 548/341; 548/373; 260/326.42
[58] Field of Search .......... 260/308 D, 30 RR, 326.4, 260/326.42; 548/253, 373, 262, 341

[56] References Cited

U.S. PATENT DOCUMENTS

| 3,004,959 | 10/1961 | Finnegan et al. | 548/252 |
|---|---|---|---|
| 3,442,945 | 5/1969 | Olin | 71/88 |
| 3,637,847 | 1/1972 | Olin | 71/118 |

FOREIGN PATENT DOCUMENTS 1227144  4/1971  United Kingdom .

OTHER PUBLICATIONS

Henry et al. JACS, 76, 923 & 924, (1954).

*Primary Examiner*—Donald G. Daus
*Assistant Examiner*—D. B. Springer
*Attorney, Agent, or Firm*—Keil & Witherspoon

[57] ABSTRACT

A process for the preparation of acetanilides by reacting 2-halo-N-halomethylacetanilides with azoles in a two-phase system, in the presence or absence of a phase transfer catalyst.

9 Claims, No Drawings

PREPARATION OF ACETANILIDES

The present invention relates to a process for the preparation of acetanilides by reacting 2-halo-N-halomethylacetanilides with azoles in a two-phase system in the presence or absence of a phase transfer catalyst.

It is known (from U.S. Pat. No. 3,637,847 (page 5, line 14) and from German Laid-Open Application DOS No. 1,542,956 (pages 5 and 6)) that the halogen atoms in the N-halomethyl group of 2-halo-N-halomethylacetanilides are very reactive and hydrolyze with water at temperatures as low as room temperature (20° C.) or below.

It is also known (from U.S. Pat. No. 3,442,945 and German Published Application DAS No. 1,543,751) to carry out reactions of such 2-halo-N-halomethylacetanilides, for example with alcohols, in the absence of moisture and using anhydrous reactants.

It is also known (from German Laid-Open Applications DOS No. 2,648,008 and DOS No. 2,744,396) to prepare acetanilides containing N-methyl-azole radicals from 2-halo-N-halomethylacetanilides and azoles under anhydrous conditions. For example, an alkali metal salt of the azole is prepared under anhydrous conditions and is reacted with a 2-halo-N-halomethylacetanilide in the absence of moisture. This conventional procedure is expensive and scarcely suitable for industrial use.

We have found that an acetanilide of the general formula I

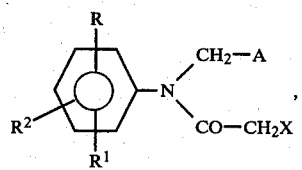

where
R is hydrogen, alkyl of up to 5 carbon atoms or alkoxy of up to 5 carbon atoms,
$R^1$ is hydrogen, halogen, alkyl of up to 5 carbon atoms, alkoxy of up to 5 carbon atoms or perhaloalkyl of up to 5 carbon atoms,
$R^2$ is hydrogen, halogen, alkyl of up to 5 carbon atoms or alkoxy of up to 5 carbon atoms, or $R^2$ together with R is alkylene of up to 6 carbon atoms, which may or may not be substituted by alkyl of up to 4 carbon atoms, and is ortho-bonded to the benzene ring,
X is chlorine or bromine, and
A is an azolyl radical which is bonded via a ring nitrogen and may be monosubstituted or polysubstituted by halogen, phenyl, alkyl, alkoxy, alkylthio or perfluoroalkyl each of up to 4 carbon atoms, cyano or carboalkoxy of up to 4 carbon atoms, is obtained in a simple manner if a 2-halo-N-halomethylacetanilide of the general formula II

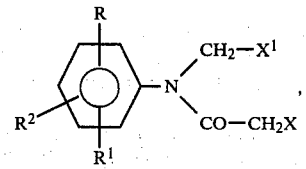

where R, $R^1$, $R^2$ and X have the above meanings and $X^1$ has the same meanings as X, and X and $X^1$ may be identical or different, is reacted with an at least molar amount of an azole of the formula H-A, where A has the above meanings, in the presence of an at least molar amount of an aqueous alkali, in a two-phase system, in the presence of absence of a phase transfer catalyst.

Some of the 2-halo-N-halomethylacetanilides of the general formula II used as starting materials are known from German Published Application DAS No. 1,542,956. Others may be prepared similarly by reacting the corresponding azomethine with a haloacetyl halide.

The 1-H-azole of the general formula H-A is advantageously used in an amount of at least one mole and at most two moles per mole of 2-halo-N-halomethylacetanilide.

Preferred 1-H-azoles of the general formula H-A are the following compounds: 2,6-dimethylpyrrole, tetramethylpyrrole, pyrazole, 3(5)-methylpyrazole, 4-methylpyrazole, 4(5)-ethylpyrazole, 4-ethylpyrazole, 3(5)-isopropylpyrazole, 4-isopropylpyrazole, 3,5-dimethylpyrazole, 3,5-dimethyl-4-acetylpyrazole, 3,5-dimethyl-4-propionylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)-chloropyrazole, 4-chloropyrazole, 4-bromopyrazole, 4-iodopyrazole, 3,4,5-trichloropyrazole, 3,4,5-tribromopyrazole, 3,5-dimethyl-4-chloropyrazole, 3,5-dimethyl-4-bromopyrazole, 4-chloro-3(5)-methylpyrazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3)-trifluoromethylpyrazole, 3,5-bistrifluoromethylpyrazole, 3(5)-methyl-5(3)-carbethoxypyrazole, 3,5-biscarbethoxypyrazole, 3,4,5-triscarbethoxypyrazole, 3(5)-methyl-5(3)-methylthio-4-carbethoxypyrazole, 4-methyl-3,5-biscarbethoxypyrazole, 4-cyanopyrazole, 4-methoxy-3,5-dichloropyrazole, triazole (sym. triazole), 3(5)-methyl-1,2,4-triazole, 3,5-dimethyl-1,2,4-triazole, 3(5)-chloro-1,2,4-triazole, 3(5)-bromo-1,2,4-triazole, 3(5)-chloro-5(3)-methyl-1,2,4-triazole, 3,5-dichloro-1,2,4-triazole, 3,5-dibromo-1,2,4-triazole, 3,5-dibromo-1,2,4-triazole, 3(5)-chloro-5(3)-cyano-1,2,4-triazole, 3(5)-chloro-5(3)-phenyl-1,2,4-triazole, 3(5)-chloro-5(3)-carbomethoxy-1,2,4-triazole, 3(5)-methyl-thio-1,2,4-triazole, 1,2,3-triazole, 4(5)-methyl-1,2,3-triazole, 4,5-dimethyl-1,2,3-triazole, 4(5)-phenyl-1,2,3-triazole, 4(5)-chloro-1,2,3-triazole, ethyl 1,2,3-triazol-4(5)-yl carboxylate, dimethyl 1,2,3-triazol-4,5-yl dicarboxylate, 5-methyltetrazole, 5-chlorotetrazole, ethyl tetrazol-5-yl carboxylate, imidazole, 2-methylimidazole, 4(5)-chloroimidazole, 2-chloroimidazole, 4,5-dichloroimidazole, trichloroimidazole, 2-methyl-4,5-dichloroimidazole, 2-ethyl-4,5-dichloroimidazole, 2-isopropyl-4,5-dichloroimidazole, 4(5)-bromoimidazole, 4,5-dibromoimidazole, tribromoimidazole, 2-methyl- 4,5-dibromoimidazole and 2-bromo-4,5-dichloroimidazole.

A two-phase system for the purposes of the invention is a mixture of water and a water-immiscible organic solvent. These liquids contain the chemical compounds in solution or dispersion.

The hydrogen halide $HX^1$ liberated during the reaction according to the invention in the two-phase system is bonded by aqueous alkalis, for example sodium hydroxide solution, potassium hydroxide solution, sodium carbonate solution, potassium carbonate solution or a solution or dispersion of $Ca(OH)_2$. The aqueous alkalis are used in an amount of at least one mole and at most, for example, in an excess of two moles, per mole of 2-halo-N-halomethylacetanilide.

Suitable organic phases for carrying out the two-phase reaction are organic solvents which are inert under the reaction conditions and are immiscible with the aqueous phase, for example aliphatic or aromatic hydrocarbons, e.g. naphtha, cyclohexane, benzene, toluene and xylenes, aliphatic or aromatic halohydrocarbons, e.g. methylene chloride, chloroform, carbon tetrachloride, chlorobenzene and dichlorobenzenes, ethers, e.g. diethyl ether, diisopropyl ether, anisole and phenetole, and esters, for example ethyl acetate and butyl acetate.

The temperatures to be maintained during the reaction are, for example, from −30° to +100° C., preferably from −10° to +50° C., especially room temperature (20° C.). The reaction is, for example, carried out under atmospheric pressure (1 bar).

To achieve a good yield and high purity of the end product, it is advantageous to prevent the 2-halo-N-halomethylacetanilide starting material from hydrolizing with water by adding a phase transfer catalyst in an amount of 0.01–30 mole percent, based on the 2-halo-N-halomethylacetanilide.

Suitable phase transfer catalysts are onium compounds, for example quaternary ammonium compounds, e.g. tetrabutylammonium chloride, tetrabutylammonium bromide, tetrabutylammonium bisulfate, tetrapentylammonium chloride, tetraoctylammonium chloride, tripropylbutylammonium chloride, tricaprylmethylammonium chloride, hexadecyltrimethylammonium chloride, distearyldimethylammonium chloride, dibenzyldimethylammonium methyl-sulfate, dimethyldodecylbenzylammonium chloride, benzyltrimethylammonium chloride, benzyltriethylammonium chloride and 2-hydroxyethyltrimethylammonium chloride, and quaternary phosphonium compounds, e.g. tributylmethylphosphonium bromide, hexadecyltributylphosphonium bromide, ethyltriphenylphosphonium bromide, tetraphenylphosphonium bromide and the corresponding hydroxides of these onium compounds.

The onium compounds can also be bonded to a solid carrier (Synthesis (1978), 315, J. org. Chem. 42 (1977), 875–879).

Further phase transfer catalysts which can be used are macrocyclic heterocyclic compounds, preferably macrocyclic polyethers, as described in Synthesis (1976), 168–188, e.g. 15-crown-5, 18-crown-6, dibenzo-18-crown-6 and dicyclohexyl-18-crown-6 ethers.

Further suitable phase transfer catalysts for carrying out the process in accordance with the invention are polyethylene glycol dialkyl ethers of a certain chain length (German Laid-Open Application DOS No. 2,534,851, and Synthesis (1977), 184–186).

Other suitable phase transfer catalysts are surfactants (tensides) as defined in Kirk-Othmer "Encyclopedia of Chemical Technology", 2nd edition, volume 19 (1969), page 508. The surfactants are preferably nonionic and are, for example, poly-alkyleneoxy derivatives. They can be prepared by reacting one mole of a higher alcohol or alkylphenol or fatty acid with from 1 to 50 units of ethylene oxide or propylene oxide. The concentration of the azole in the aqueous phase is, for example, from 5 to 60% by weight. The concentration of the alkali in the aqueous phase is, for example, from 5 to 30% by weight. The concentration of the 2-halo-N-halomethylacetanilide in the organic phase is, for example, from 5 to 40% by weight.

The reaction is advantageously carried out with thorough mixing of the two phases, for example by vigorous stirring. In carrying out the process according to the invention it is immaterial whether the organic phase, containing the 2-halo-N-halomethylacetanilide, is initially introduced into the reaction vessel and the aqueous phase containing the azole and the aqueous alkali is added with thorough mixing, or whether the said aqueous phase is first introduced and the organic phase is added; both these methods constitute batchwise processes. It is equally possible to introduce the two phases simultaneously from two metering devices into an inert organic solvent or into an unpurified solution of technical-grade azolyl-acetanilide, the mixing of the two phases taking place in a mixing loop or a mixing zone. After separating off the aqueous phase, which essentially is an alkali metal halide solution, especially if stoichiometric amounts of starting materials have been used, and after removing a part of the organic phase, the remainder of the organic phase can be returned to the mixing loop. This constitutes a continuous process.

The phase transfer catalyst can be added to the organic phase or to the aqueous alkaline phase, but in the batchwise method it is advantageous to add the phase transfer catalyst to the phase initially introduced into the reaction vessel.

If unsymmetrically substituted azoles, for example monosubstituted, disubstituted or trisubstituted pyrazoles or imidazoles or 1,2,3-triazoles or 1,2,4-triazoles are used as the starting materials, the tautomeric structures of the starting materials of the general formula H-A result, in the preparation according to the invention of the acetanilides of the general formula I, in two isomers of the formulae shown below, the ratio of which is essentially determined by the nature of the radicals (B, C, D in, for example, the pyrazole).

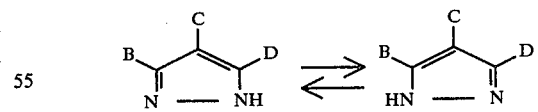

The Examples which follow illustrate the process according to the invention without implying a limitation. Parts by volume bear the same relation to parts by weight as that of the liter to the kilogram.

EXAMPLE 1

A solution of 13.7 parts by weight of 4,5-dichloroimidazole and 4.4 parts by weight of sodium hydroxide in 20 parts of water was added dropwise to a solution of 24.6 parts by weight of 2-chloro-N-chloromethyl-2',6'-dimethylacetanilide and 2.0 parts by weight of triethylbenzylammonium chloride in 50 parts by volume of dichloromethane at 20°–25° C., with vigorous stirring, which was continued for 2 hours. The organic phase was washed with three times 30 parts by volume of water, dried over sodium sulfate and evaporated under reduced pressure at 70° C., to give 29.9 parts by weight of 2-chloro-2',6'-dimethyl-N-(4,5-dichloroimidazol-1-yl-methyl)-acetanilide of melting point 99° C.; the product was pure according to the $^1$H-NMR spectrum and according to thin layer chromatography carried out with a 3:7 ethyl acetate:toluene mixture.

EXAMPLE 2

A solution of 9.0 parts by weight of 4-methylpyrazole and 4.0 parts by weight of sodium hydroxide in 20 parts by volume of water was added dropwise at 0° C., with vigorous stirring, to a solution of 24.6 parts by weight of 2-chloro-N-chloromethyl-2',6'-dimethylacetanilide and 0.15 part by weight of tri-n-butylmethylphosphonium bromide in 80 parts by volume of o-dichlorobenzene, and the stirring was continued for 5 hours at 10° C. The organic phase was washed with three times 50 parts by volume of water, dried over sodium sulfate and evaporated under reduced pressure at 70° C. to give 25.6 parts by weight of 2-chloro-2',6'-dimethyl-N-(4-methylpyrazol-1-yl-methyl)-acetanilide of melting point 100° C.; the product was pure according to the $^1$H-NMR spectrum and according to thin layer chromatography carried out using a 3:7 ethyl acetate:toluene mixture.

EXAMPLE 3

A solution of 10.8 parts by weight of 4-methoxypyrazole and 4.0 parts by weight of sodium hydroxide in 20 parts by volume of water was added dropwise at 10°–15° C., with vigorous stirring, to a solution of 24.6 parts by weight of 2-chloro-N-chloromethyl-2',6'-dimethylacetanilide and one part by weight of benzyltriethylammonium bromide in 70 parts by volume of toluene and the stirring was continued for 3 hours. The organic phase was washed with three times 40 parts by volume of water, dried over sodium sulfate and evaporated in vacuo at 80° C. to give 28.1 parts by weight of 2-chloro-2',6'-dimethyl-N-(4-methoxypyrazol-1-yl-methyl)acetanilide of melting point 115°–116° C. (melting point of a sample recrystallized from ethanol: 118° C.), which according to the $^1$H-NMR spectrum and thin layer chromatography carried out using a 3:7 mixture of ethyl acetate:toluene was more than 97% pure.

EXAMPLE 4

A solution of 12.1 parts by weight of 4-isopropylpyrazole and 5.6 parts by weight of potassium hydroxide in 30 parts by volume of water was added at 25° C., with vigorous stirring, to a solution of 24.6 parts by weight of 2-chloro-N-chloromethyl-2',6'-dimethylacetanilide and 0.5 part by weight of triethylbenzylammonium chloride in 100 parts by volume of chloroform and stirring was continued for 4 hours at 25° C. The organic phase was washed with three times 50 parts by volume of water, dried over sodium sulfate and evaporated under reduced pressure at 50° C. to give 26.2 parts by weight of 2-chloro-2',6'-dimethyl-N-(4-isopropylpyrazol-1-yl-methyl)-acetanilide of melting point 58° C.

EXAMPLE 5

A solution of 27.4 parts by weight of 1,2,4-triazole and 11.2 parts by weight of potassium hydroxide in 50 parts by volume of water was added dropwise, at room temperature, to a solution of 49.2 parts by weight of 2-chloro-N-chloromethyl-2',6'-dimethylacetanilide and 6.2 parts by weight of tetrabutylammonium bisulfate in 200 parts by volume of methylene chloride and the mixture was stirred vigorously for 5 hours. The organic phase was washed with three times 80 parts by volume of water and dried over sodium sulfate, and the solvent was evaporated under reduced pressure at 60° C. to give 46.1 parts by weight of a crystalline mass which contained 88% of 2-chloro-2',6'-dimethyl-N-(1,2,4-triazol-1-yl-methyl)-acetanilide of melting point 115°–118° C. and 10% of 2-chloro-2',6'-dimethylacetanilide of melting point 140°–143° C. (the compounds being separated by column chromatography on silica gel, using methylene chloride as the eluant).

EXAMPLE 6

A solution of 7.5 parts by weight of pyrazole and 4.0 parts by weight of sodium hydroxide in 20 parts by volume of water was added dropwise at 20°–25° C., with vigorous stirring, to a solution of 24.6 parts by weight of 2-chloro-N-chloromethyl-2',6'-dimethylacetanilide and M parts by weight of phase transfer catalyst in 70 parts by volume of toluene, and stirring was continued for 3–5 hours at the same temperature. After complete conversion (checked by thin layer chromatography), the organic phase was washed three times with water, dried and concentrated under reduced pressure at 70° to give G parts by weight of 2-chloro-2',6'-dimethyl-N-(pyrazol-1-yl-methyl)-acetanilide, as shown in the Table which follows.

| Experiment No. | Phase transfer catalyst | M | G | (% of theory) | Melting point (°C.) | Purity (%) (NMR) |
|---|---|---|---|---|---|---|
| 1 | Tetrabutylammonium iodide | 0.37 | 24.3 | (87.6) | 78 | 98 |
| 2 | Triethylbenzylammonium chloride | 0.20 | 26.1 | (94.3) | 78 | 96 |
| 3 | Tributylmethylphosphonium bromide | 0.30 | 25.0 | (90.4) | 77 | 95 |
| 4 | Distearyldimethylammonium chloride | 0.59 | 25.5 | (92.0) | 78 | 97 |
| 5 | Trimethyl—$C_{13}$/$C_{15}$—alkylammonium chloride | 0.29 | 23.5 | (85.0) | 76 | 96 |
| 6 | Dibenzyldimethylammonium methyl-sulfate | 0.34 | 25.2 | (91.0) | 76 | 95 |
| 7 | Dimethyl—$C_{12}$/$C_{14}$—alkylbenzylammonium chloride | 0.35 | 24.4 | (88.0) | 78 | 95 |
| 8 | Tetrabutylammonium hydroxide | 0.26 | 25.2 | (91.0) | 75 | 94 |
| 9 | 18-Crown-6 ether | 0.26 | 24.8 | (90.0) | 77 | 97 |
| 10+ | Triethylbenzylammonium chloride | 0.05 | 26.2 | (94.6) | 78 | 97 |

| Experiment No. | Phase transfer catalyst | M | G | (% of theory) | Melting point (°C.) | Purity (%) (NMR) |
| --- | --- | --- | --- | --- | --- | --- |
| 11+ | No catalyst | — | 25.3 | (91) | 70 | 90 |

+Methylene chloride instead of toluene.

EXAMPLE 7

4.0 parts by weight of sodium hydroxide and 0.2 part by weight of triethylbenzylammonium chloride were added to 51.0 parts by weight of a 14.7 percent strength aqueous pyrazole solution containing 12–13 percent of sodium chloride, the solution having been prepared by cleavage of 1,1,3,3-tetramethoxypropane with a solution of hydrazine in hydrochloric acid, evaporation of the resulting methanol under reduced pressure and subsequent neutralization (Org. Prep. Proced. Int. 5 (1973) 3, 141). A solution of 24.6 parts by weight of 2-chloro-N-chloromethyl-2',6'-dimethylacetanilide in 100 parts by volume of toluene was added dropwise in the course of 30 minutes at 20°–25° C., with vigorous stirring, and the stirring was continued for 3 hours. 23.5 parts by weight of 2-chloro-2',6'-dimethyl-(N-pyrazol-1-yl-methyl)-acetanilide of melting point 78° C. ($^1$H-NMR analysis: 95% pure) was isolated from the toluene phase by the method described in Example 6.

We claim:
1. A process for the preparation of an acetanilide of the formula I

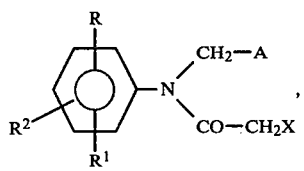

where
R is alkyl of up to 5 carbon atoms,
$R^1$ is alkyl of up to 5 carbon atoms
$R^2$ is hydrogen,
X is chlorine or bromine, and
A is an imidazolyl, pyrrolyl, pyrazolyl, triazolyl, or tetrazolyl group which is bonded via a ring nitrogen and may be monosubstituted, disubstituted or trisubstituted on its ring members by halogen, phenyl, methyl, ethyl, isopropyl, methoxy, trifluoromethyl, or cyano, wherein a 2-halo-N-halomethylacetanilide of the general formula II

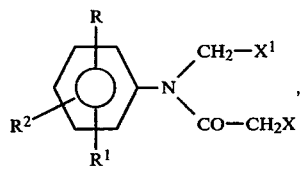

where R, $R^1$, $R^2$ and X have the above meanings and $X^1$ has the same meanings as X, and X and $X^1$ may be identical or different, is reacted at −30° C. up to 100° C. with an at least one molar amount of azole of the formula H-A per mole of said acetanilide, where A has the above meanings, in the presence of an at least one molar amount of an aqueous alkali per mole of said acetanilide, in a water immiscible liquid organic solvent-aqueous two-phase system with vigorous agitation of the two-phase system.

2. A process as claimed in claim 1, wherein a phase transfer catalyst is added to the two-phase system.

3. A process as claimed in claim 1, wherein said azole of the formula H-A is one of the the following compounds: 2,6-dimethylpyrrole, tetramethylpyrrole, pyrazole, 3(5)-methylpyrazole, 4-methylpyrazole, 4(5)-ethylpyrazole, 4-ethylpyrazole, 3(5)-isopropylpyrazole, 4-isopropylpyrazole, 3,5-dimethylpyrazole, 3,5-dimethyl-4-acetylpyrazole, 3,5-dimethyl-4-propionylpyrazole, 3,4,5-trimethylpyrazole, 3(5)-phenylpyrazole, 4-phenylpyrazole, 3,5-diphenylpyrazole, 3(5)-phenyl-5(3)-methylpyrazole, 3(5)-chloropyrazole, 4-chloropyrazole, 4-bromopyrazole, 4-iodopyrazole, 3,4,5-trichloropyrazole, 3,4,5-tribromopyrazole, 3,5-dimethyl-4-chloropyrazole, 3,5-dimethyl-4-bromopyrazole, 4-chloro-3(5)-methylpyrazole, 4-bromo-3(5)-methylpyrazole, 4-methyl-3,5-dichloropyrazole, 3(5)-methyl-4,5(3)-dichloropyrazole, 3(5)-chloro-5(3)-methylpyrazole, 4-methoxypyrazole, 3(5)-methyl-5(3)-methoxypyrazole, 3(5)-ethoxy-4,5(3)-dimethylpyrazole, 3(5)-methyl-5(3)-trifluoromethylpyrazole, 3,5-bistrifluoromethylpyrazole, 3(5)-methyl-5(3)-carbethoxypyrazole, 3,5-biscarbethoxypyrazole, 3,4,5-triscarbethoxypyrazole, 3(5)-methyl-5(3)-methylthio-4-carbethoxypyrazole, 4-methyl-3,5-biscarbethoxypyrazole, 4-cyanopyrazole, 4-methoxy-3,5-dichloropyrazole, triazole (sym. triazole), 3(5)-methyl-1,2,4-triazole, 3,5-dimethyl-1,2,4-triazole, 3(5)-chloro-1,2,4-triazole, 3(5)-bromo-1,2,4-triazole, 3(5)-chloro-5(3)-methyl-1,2,4-triazole, 3,5-dichloro-1,2,4-triazole, 3,5-dibromo-1,2,4-triazole, 3,5-dibromo-1,2,4-triazole, 3(5)-chloro-5(3)-cyano-1,2,4-triazole, 3(5)-chloro-5(3)-phenyl-1,2,4-triazole, 3(5)-chloro-5(3)-carbomethoxy-1,2,4-triazole, 3(5)-methyl-thio-1,2,4-triazole, 1,2,3-triazole, 4(5)-methyl-1,2,3-triazole, 4,5-dimethyl-1,2,3-triazole, 4(5)-phenyl-1,2,3-triazole, 4(5)-chloro-1,2,3-triazole, ethyl 1,2,3-triazol-4(5)-yl carboxylate, dimethyl 1,2,3-triazol-4,5-yl dicarboxylate, 5-methyltetrazole, 5-chlorotetrazole, ethyl tetrazol-5-yl carboxylate, imidazole, 2-methylimidazole, 4(5)-chloroimidazole, 2-chloroimidazole, 4,5-dichloroimidazole, trichloroimidazole, 2-methyl-4,5-dichloroimidazole, 2-ethyl-4,5-dichloroimidazole, 2-isopropyl-4,5-dichloroimidazole, 4(5)-bromoimidazole, 4,5-dibromoimidazole, tribromoimidazole, 2-methyl-4,5-dibromoimidazole and 2-bromo-4,5-dichloroimidazole.

4. A process as claimed in claim 3, wherein a phase transfer catalyst is added to the two-phase system.

5. A process as claimed in claim 1, wherein A is said imidazolyl group.

6. A process as claimed in claim 1, wherein A is said pyrazolyl group.

7. A process as claimed in claim 1, wherein A is said triazolyl group.

8. A process as claimed in claim 3, wherein the process is carried out to a temperature in the range of −10° C. up to 50° C.

9. A process as claimed in claim 1, wherein the process is carried out to a temperature in the range of −10° C. up to 50° C.

* * * * *